(12) United States Patent
Leijssen et al.

(10) Patent No.: US 11,841,133 B2
(45) Date of Patent: Dec. 12, 2023

(54) ANTIFOULING SYSTEM WITH INDUCTIVE POWER TRANSFER FOR USE IN PROTECTING A SURFACE AGAINST BIOFOULING

(71) Applicant: KONINKLIJKE PHILIPS N.V., Eindhoven (NL)

(72) Inventors: Jacobus Josephus Leijssen, Waare (NL); Martijn Gerarda Lambertus Justinus Van Uden, Eindhoven (NL)

(73) Assignee: Koninklijke Philips N.V., Eindhoven (NL)

( * ) Notice: Subject to any disclaimer, the term of this patent is extended or adjusted under 35 U.S.C. 154(b) by 369 days.

(21) Appl. No.: 17/277,779

(22) PCT Filed: Sep. 18, 2019

(86) PCT No.: PCT/EP2019/075000
§ 371 (c)(1),
(2) Date: Mar. 19, 2021

(87) PCT Pub. No.: WO2020/058332
PCT Pub. Date: Mar. 26, 2020

(65) Prior Publication Data
US 2021/0346922 A1 Nov. 11, 2021

(30) Foreign Application Priority Data
Sep. 20, 2018 (EP) .................................. 18195677

(51) Int. Cl.
*B63B 59/08* (2006.01)
*B63B 59/04* (2006.01)
(Continued)

(52) U.S. Cl.
CPC ................ *F21V 31/00* (2013.01); *A61L 2/08* (2013.01); *A61L 2/10* (2013.01); *A61L 2/26* (2013.01);
(Continued)

(58) Field of Classification Search
CPC ........ A61L 2/10; A61L 2202/11; B08B 17/02; B63B 59/04; B63B 59/06; B63B 59/08;
(Continued)

(56) References Cited

U.S. PATENT DOCUMENTS 5,643,424 A 7/1997 Riffe et al.
9,051,028 B2 6/2015 Smith et al.
(Continued)

FOREIGN PATENT DOCUMENTS

CN 101709191 B 8/2011
CN 107124041 A 9/2017
(Continued)

OTHER PUBLICATIONS

International Search Report and Written Opinion from PCT/EP2019/075000 dated Mar. 26, 2020.

*Primary Examiner* — Levi Gannon

(57) ABSTRACT

An antifouling system for reducing and/or preventing fouling of an object exposed to fouling conditions when in use, comprising a plurality of antifouling devices (26) for providing an antifouling radiation to at least part of the object and/or at least part of the antifouling system; wherein the antifouling system further comprises: —a power transmission system comprising: —an inductive power emitter (10) comprising at least one inductive emitter element (12); and —a plurality of inductive power receivers (24) each one comprising at least one inductive receiver element; wherein the inductive power emitter and the plurality of inductive power receivers are for mounting on the object in a fixed (Continued)

configuration with respect to each other thereby to provide an inductive coupling between each one of the at least one inductive receiver elements and the at least one inductive emitter element such that power may be inductively transmitted when the power transmission system is in use; and wherein the plurality of antifouling devices (26) are configured to be driven using transmitted power from at least one of the plurality of inductive power receivers when the system is in use.

20 Claims, 4 Drawing Sheets

(51) Int. Cl.

| | |
|---|---|
| *A61L 2/10* | (2006.01) |
| *C09D 5/16* | (2006.01) |
| *H02J 50/10* | (2016.01) |
| *H02J 50/40* | (2016.01) |
| *F21V 31/00* | (2006.01) |
| *F21V 23/02* | (2006.01) |
| *F21V 23/04* | (2006.01) |
| *B08B 17/02* | (2006.01) |
| *A61L 2/08* | (2006.01) |
| *A61L 2/26* | (2006.01) |
| *C09D 5/06* | (2006.01) |
| *F21W 107/20* | (2018.01) |
| *H02J 50/90* | (2016.01) |
| *H05B 45/50* | (2022.01) |

(52) U.S. Cl.
CPC ............. *B08B 17/02* (2013.01); *B63B 59/08* (2013.01); *C09D 5/06* (2013.01); *F21V 23/02* (2013.01); *F21V 23/0442* (2013.01); *H02J 50/10* (2016.02); *H02J 50/402* (2020.01); *A61L 2202/11* (2013.01); *B63B 59/04* (2013.01); *F21W 2107/20* (2018.01); *H02J 50/90* (2016.02); *H05B 45/50* (2020.01)

(58) Field of Classification Search
CPC ... C09D 5/16; H02J 50/10; H02J 50/12; H02J 50/40; H02J 50/402; H02J 50/90
See application file for complete search history.

(56) References Cited

U.S. PATENT DOCUMENTS

| | | | |
|---|---|---|---|
| 10,436,437 B1* | 10/2019 | Usher | F21V 3/06 |
| 2009/0206674 A1* | 8/2009 | Noguchi | A61L 2/24 |
| | | | 307/104 |
| 2013/0181535 A1* | 7/2013 | Muratov | H02J 50/10 |
| | | | 307/104 |
| 2013/0334960 A1 | 12/2013 | Waffenschmidt et al. | |
| 2017/0048934 A1 | 2/2017 | Sempel et al. | |
| 2017/0190397 A1 | 7/2017 | Salters et al. | |
| 2017/0334114 A1 | 11/2017 | Sticklus et al. | |
| 2019/0084015 A1* | 3/2019 | Woelk | G02B 19/0095 |
| 2019/0207429 A1 | 7/2019 | Yoshida et al. | |
| 2019/0014631 A1 | 10/2019 | Van Delden et al. | |
| 2020/0183119 A1* | 6/2020 | deWijs | G02B 1/18 |

FOREIGN PATENT DOCUMENTS

| | | |
|---|---|---|
| JP | 2006339044 A | 12/2006 |
| WO | 2014060921 A1 | 4/2014 |
| WO | 2014188347 A1 | 11/2014 |
| WO | 2017108641 A1 | 6/2017 |
| WO | 2018069330 A1 | 4/2018 |

* cited by examiner

ANTIFOULING SYSTEM WITH INDUCTIVE POWER TRANSFER FOR USE IN PROTECTING A SURFACE AGAINST BIOFOULING

CROSS REFERENCE TO RELATED APPLICATIONS

This application is a U.S. national phase application of International Application No. PCT/EP2019/075000 filed on Sep. 18, 2019, which claims the benefit of EP Application Serial No. 18195677.2 filed on Sep. 20, 2018 and are incorporated herein by reference.

FIELD OF THE INVENTION

The present disclosure relates to antifouling systems having inductive power transfer systems for powering a load of the antifouling system. The disclosure further relates to an object subject to fouling when in use and having such antifouling system.

BACKGROUND OF THE INVENTION

Biofouling or biological fouling is the accumulation of microorganisms, plants, algae, and/or animals on surfaces and especially those that are exposed to moist or watery environment such as sea, lake or river. The variety among biofouling organisms is highly diverse and extends far beyond attachment of barnacles and seaweeds. According to some estimates, over 1700 species comprising over 4000 organisms are responsible for biofouling. Biofouling is divided into microfouling which includes biofilm formation and bacterial adhesion, and macrofouling which is the attachment of larger organisms. Due to the distinct chemistry and biology that determine what prevents organisms from settling, these organisms are also classified as hard or soft fouling types.

Calcareous (hard) fouling organisms include barnacles, encrusting bryozoans, mollusks, polychaete and other tube worms, and zebra mussels. Examples of non-calcareous (soft) fouling organisms are seaweed, hydroids, algae and biofilm "slime". Together, these organisms form a fouling community.

In several circumstances, biofouling creates substantial problems such as for example. Machinery stops working, water inlets get clogged, and hulls of ships suffer from increased drag and thus increased fuel consumption. It is estimated that an increase of up to 40% in fuel consumption can be attributed to biofouling. As large oil tankers or container transport ships can consume up to €200,000 a day in fuel, substantial savings are possible with an effective method of antifouling. Hence the topic of antifouling, i.e. the process of removing or preventing fouling from forming, is well known.

In industrial processes, bio-dispersants can be used to control biofouling. In less controlled environments, organisms are killed or repelled with coatings using biocides, thermal treatments or pulses of energy. Nontoxic mechanical strategies that prevent organisms from attaching include choosing a material or coating with a slippery surface, or creation of nanoscale surface topologies similar to the skin of sharks and dolphins which only offer poor anchor points.

WO 2014/188347 discloses a system for preventing biofouling in which all of a surface, or a significant amount of a surface, to be kept clean from fouling (e.g. the hull of a ship) is covered with a layer that emits germicidal light, in particular UV light. Thus, it is known to adopt a light based method, in particular using ultra-violet (UV) light to reduce or prevent fouling. It is well-known that most micro-organisms are killed, rendered inactive or unable to reproduce with sufficient UV light. This effect is mainly governed by the total dose of UV light. A typical dose to kill 90% of a certain micro-organism is 10 mW-hours per square meter. A particularly effective type of light in this respect is UVC light with a wavelength in the approximate wavelength range of 100 to 280 nm. In WO 2014/188347 lower power UV LEDs are used to provide the necessary UV light. LEDs can generally be included in small packages and consume less power than other types of light sources. LEDs can be manufactured to emit (UV) light of various desired wavelengths and their operating parameters, most notably the output power, can be controlled to a high degree. A suitable germicidal dose can easily be achieved with existing UV LEDs.

SUMMARY OF THE INVENTION

In the know system it is necessary to deliver power to the light sources disposed in the layer applied to the ship. This is problematic in the sense that the system needs to be designed so that it allows application to a large irregularly shaped surface of an object (e.g. a ships hull) and is operable in conditions where it is at least partly submerged in water potentially giving rise to electrical hazards as well as issues of corrosion.

There is therefore a need for an improved antifouling system that is electrically powered.

It is an object of the invention to at least partly foresee in the aforementioned need.

It was realized by the inventors that the aforementioned conditions under which such system must be applied and operated require a number of design choices to be made in order to cope with such conditions. A single element system with protected galvanic power provision circuitry would be preferred. But such system will be really difficult to design and mount to a large object.

According to a first aspect of the invention there is provided an antifouling system as defined in the claims.

The inventors have recognized that an antifouling system with a modular design including multiple antifouling panels for covering an area of a surface of an object would at least partly fulfill the aforementioned object. In particular this would allow to cover a large surface of an object (e.g. a ship's hull) by applying the antifouling panels to different areas of such surface. This will not only make mounting of the system easier, but will make the system more flexible in terms of shape (e.g. curved) and sizes of surfaces that can be covered. In order to make such a system a robustly operating one, the power provision strategy was chosen to be partly based on wireless power transfer with the power transmission system as defined in the claims. With such transfer system a central power inductive power emitter may be used to provide power to multiple inductive power receivers. Thus each panel can have one such receiver and thus be powered by the central inductive power emitter. This provides an effective way to deliver power to a load (plurality of antifouling devices) which extends over a large area. In particular, a grid of at least one and preferably more power delivery transmitters each one associated with multiple power receiving panels may be formed, to cover a large area. The inductive power receivers and transmitter(s) may be encapsulated in panels so that they are protected against the environmental conditions (e.g. water). Thus corrosion problems may be reduced while power can be transferred as needed. Furthermore, central power provision from a power source (e.g. ships generators or batteries or the like) to the inductive power emitter(s) may be established above the waterline of the object, so that galvanic connections may be used for this purpose without introducing e.g. problems of corrosion, while power transfer below the waterline can occur wirelessly. The use of wireless power transfer using inductive elements such as coils not only simplifies making a watertight arrangement by encapsulation with no openings to the environment, but also makes application of the antifouling system easier. After all, slight differences in alignment of emitter and receiver elements of different across a generally irregular surface of an object, which would otherwise lead to differences in power transfer, can be tolerated to some extent with such inductive design.

With the power transfer system, the antifouling devices can be provided with power to be driven to provide the antifouling radiation. The driving need not be continuous during use of the antifouling system. The driving may be periodic. In some embodiments all of the transferred power is used for this driving. In other embodiments only part of this power is used to drive the antifouling devices. Thus in such cases there may be more power transferred than needed for the driving of the antifouling devices. Hence other devices, such as sensors or data transfer devices may be driven using the excess power. In variations to these embodiments, the power may be used to drive the antifouling devices discontinuously, i.e. during one time period, while they are not driven (or at lower power level) at another time period different from the one time period. In this non-driven period power may either cease to be transferred or it may be used for driven other devices such as sensors or data transfer systems. Such may be convenient for example when there is not enough power transferred for driving all power requiring devices at the same time.

Preferably the antifouling devices of the antifouling system comprise UV light sources and in particular comprise UV-C light sources. In such cases the UV or UV-C light provides the antifouling radiation.

The antifouling system is a modular system made of inductive power emitters and inductive power receivers physically separated from each other in which multiple receivers may be provided with power by one emitter.

In an embodiment the antifouling system comprises a first panel (power provision panel) including the inductive power emitter and a plurality of second panels (antifouling panels), separate from the first panel, each second panel comprising at least one of the plurality of inductive power receivers and at least one of the plurality of antifouling devices. The antifouling panels may cover a larger area than the power provision panels. In particular, each antifouling panel distributes the power received from the power provision panels to the antifouling devices within an antifouling panel. These devices if there are more than one are preferably distributed across the area of the antifouling panel.

Each one of the plurality of second panels preferably includes one or more water resistant materials by which any of the plurality of inductive power receivers and any of the plurality of the antifouling devices present within that particular second panel are encapsulated. The encapsulation serves to protecting the plurality of inductive power receivers and the plurality of antifouling devices against at least liquid water. Protection entails at last partial but preferably entire shielding from environmental water such as sea water. This may reduce corrosion and short circuit problems of the receivers and antifouling devices when the system is used in watery conditions, after all they are electrical devices susceptible to such deteriorations. One example of water resistant materials comprise silicone polymers. Another comprises fluoroethylene polymers (FEP). The encapsulation may take many forms, one of which is comprises the devices embedded in at least one of the materials. The material may be one single type of material, but may also be a composite in mixed form or in layered form or both. There may thus be a system of layers for example comprising silicone polymers and FEP polymer. The devices may then be embedded in the silicone polymers while the FEP polymer serves as a further cover layer on top of the silicone polymer.

In an embodiment of the antifouling system the one or more inductive emitter elements each comprise or consist of power emitter coils and the one or more inductive receiver elements each comprise or consist of power receiver coils and the inductive power emitter and the inductive power receivers are configured such that each one of the one or more power receiver coils at least partly overlaps with at least one of the one or more power emitter coils when the system is mounted to the object. Coils can serve as efficient power transfer elements providing an internal (enclosed) cross sectional area in which magnetic field flux is concentrated to be used for inductive coupling. A coil may have one or more windings such as for example more than 2, more than 3, more than 5 windings. An emitter coil may have less or more windings than a receiver coil. A coil (emitter and/or receiver coil) may have a core for further concentrating magnetic flux, but this is not needed per se. Emitter coil and receiver coil may have a same cross sectional area or different cross sectional area. For example an emitter coil may have a larger cross sectional area than a receiver coil. This is for example advantageous when multiple receiver coils need to draw power from one and the same emitter coil.

In an embodiment each one of the plurality of inductive power receivers are configured such that the at least one power emitter element of a respective inductive power receiver element at least partly overlaps with the at least one power emitter element when the system is mounted to the object and wherein each one of the plurality of second panels comprises one or more edge regions in which its at least one power receiver element is disposed. This overlap is advantageous for optimizing the inductive coupling. Preferably any emitting or receiving elements are then coils as disclosed herein before or herein after. In case there are second panels comprising the inductive power receivers each one of the plurality of second panels comprises one or more edge regions (22) in which its at least one power receiver element is disposed. Each of the secondary panels are for example mounted over the inductive power emitter. The inductive power emitter is for example for mounting over the surface of the object and the inductive power receiver panels overlap the inductive power emitter. Thus, the power receiver elements, for example in the form of coils, take up a relatively small area of the panels and the overlap areas of panels with inductive power transmitter parts only needs to be small so that the overall system may generally be kept thin. Also the area inductive power transmitters take up, for example when part of a primary panel, may be kept small in relation to the area covered by secondary panels.

The inductive power transmitter can comprise a power feed line and a power return line for electrically connecting to the at least one power emitter element. A pair of power feed line and power return line may be referred to as a power transmission line. The inductive power emitter can be designed with a low AC transmission line impedance leading to low losses. Such line is referred to as partially or entirely balanced transmission line. To this end, the power feed line and return line may run side by side at defined constant distance along the lines with an isolator in between. They may be arranged side by side in a single layer multi conductor track setup or be arranged one on top of the other in a multi conductor layer setup. The latter may provide a nearly complete balancing of the power transmission line.

In an advantageous embodiment of the antifouling system the at least one inductive emitter elements comprises a plurality of inductive emitter elements each one electrically connected in parallel configuration to the power feed line and to the power return line and positioned in series with respect to each other within the inductive power emitter, each one of the plurality of inductive emitter elements being arranged to inductively couple to at least one of the at least one inductive receiver elements of one of the plurality of inductive power receivers. Again the emitter and receiver elements preferably are coils as defined herein after or before. Each inductive power receiver may be inductively coupled to at least one and preferably one of the power emitter elements of the inductive power emitter. Positioned in series means that the elements are spatially distributed in a side by side fashion with respect to each other such that there is at least some non-overlapping part. This is a way to deliver current to each power receiver element in an efficient way such that power receiver elements can be located side by side in an optimum alignment for covering a large surface of an object. Such system may be voltage driven. The use of emitter elements in series (which would mean the same current at all points) would make it more difficult to maintain a total voltage within a safety voltage limit, such as 50 Vrms.

The inductive power emitter may have a power feed line extending from one end of the inductive power transmitter to the at least one inductive emitter element and a power return line extending from the at least one inductive emitter element to the one end of the inductive power transmitter, wherein the power feed line and the power return line are located on one side of the at least one inductive emitter elements. Thus, for each one of a plurality of inductive emitter elements, the power feed line and the power return line are located on one side of such inductive power emitter. Preferably the lines run along the same side of the plurality of inductive power transmitters. In this way, the magnetic fields caused at the location of an inductive emitter element by the power feed line and power return line, which fields are of different strengths along the length of these lines as a result of the tapping off of current of successive coils due to the parallel electrical configuration) are at least partially or substantially cancelled, so that a more uniform magnetic field strength is achieved going from one inductive emitter element to another within an inductive power emitter.

In another arrangement of the antifouling system the inductive power emitter comprises at least one inductive emitter element for inductive coupling to a plurality of power receiver elements, the plurality of power receiving elements being comprised of the at least one power receiver elements of at least two of the plurality of inductive power receivers. Preferably the inductive power emitter comprises a single inductive emitter element for coupling to each and every one of the power receiver elements of the plurality of inductive power receivers. Thus, a single power emitter element is used to inductively couple to a set of inductive power receivers. In this way, the inductive coupling and therewith power transfer to each inductive power receiver may be the same or close to the same.

In an embodiment of the antifouling system the inductive power emitter includes a power feed line and a power return line and each one of the at least one inductive emitter elements comprises a section of the power feed line and a section of the power return line. No actual coils are now present but merely sections of the lines that are near each other to provide a sum field in between that can be used to inductively couple with a power receiver element. This is a simpler design.

In an embodiment of an antifouling system the system further comprises a further one of the inductive power emitter and at least one connection member wherein the power feed line of the inductive power emitter is connected to the power return line of the further inductive power emitter via the connection member. In such an arrangement, the system comprises a set of inductive power emitters and each one is associated with a respective plurality of inductive power receivers. Each of the inductive power transmitters comprises a power feed line and a power return line and the power feed line of one of the inductive power emitters is connected to the power return line of the further one of the inductive power transmitters.

In this design, the individual inductive power transmitters do not have a closed power transmission line. Instead, they define one half of one power emitter coil and one half of another power emitter coil. There is again one power emitter coil which extends over the full length of the strip.

Connecting members are then preferably provided between the second ends of, for example, adjacently arranged inductive power emitters, to connect the power feed line of one transmitter with the power return line of an adjacent one to one side and to connect the power return line of said one transmitter with the power feed line of an adjacent strip to the other side.

The inductive power emitter may comprise a ferrite material for example in the form of layer or sheet below the inductive emitter elements, hence between the surface of an object and the elements when the system is mounted to the object. The system efficiency can thus be kept high, e.g. close to 50% even if the surface over which the system is to be mounted is electrically conductive such as e.g. is the case with a ships metal hull. The ferrite material is between the surface, e.g. a ship's hull, and the inductive transformer primary windings, to prevent Eddy currents through the conductive layer which defines the surface. Such ferrite material may be dispensed with when the surface is made of non-conducting materials such as wood or plastic.

A coating or paint material may be provided for application to the surface, such that the system is for mounting over a layer of the coating or paint material, wherein the coating or paint material has a relative permeability ($\mu_r$) greater than 20, for example greater than 100, for example greater than 200. The coating or paint material preferably is thus located between the system and the surface.

The purpose is to prevent or attenuate the existence of Eddy currents in the hull that will lead to losses. The higher the value the better the performance. This improves the coupling factor for example even if a polyester or aluminum hull is used.

The high relative permeability for example may also give rise to a high dielectric permittivity.

This provides an alternative way to reduce Eddy currents in the metal hull (giving rise to losses) and may avoid the need for a ferrite material. The coating or paint material for example has embedded ferromagnetic particles.

The inductive power receivers for example have a thickness of less than 5 mm, for example less than 4 mm, for example less than 3 mm. This thickness typically includes a printed circuit board (PCB).

The secondary panels including the inductive power receivers may have thickness of less than 2 cm, for example less than 1.5 cm or even less than 1 cm. This may include the encapsulating material defined herein before.

The plurality of antifouling devices for example comprises one or more light sources for providing antifouling light as described herein before. The inductive power transfer system may thus be part of a light based antifouling system to be applied to the surface. The light sources may be part of a light source arrangement for example comprising an array of UV-C LEDs for emitting UV light with a wavelength between 270 nm and 280 nm.

The antifouling system can comprise a power source for delivering power to the inductive power emitter. The power source for example comprises a resonant circuit with a resonant frequency of 50 kHz to 1 MHz, for example 50 kHz to 200 kHz, for example 60 kHz to 90 kHz.

The inductive power receivers and the inductive power transmitters may be comprised in respective first and second panels each of these including a silicone material having a protective function and optionally also an optical function, e.g. light guiding.

A second panel may have many shapes such as triangular or rectangular. They may have an area of 0.5 m² or larger. Preferably they have an area of 2.5 m² or larger. The sides of such panels may be of dimensions (length and width) larger than 0.1 or 0.2 meter, preferably larger than 0.5 meter. Not all sides of a panel, or of different panels in case there are more in a system, need to have the same dimensions.

The shapes and sizes (area) or dimensions (length, width) of the first panels may be any as long as suitable for use in an antifouling system to be able to protect ore even cover the surface. They shapes and sizes may be chosen according to size and shape of the surface they need to be applied to. Since the surface preferably is one of a marine object such as vessel, ship etc., such surfaces are in general quite large, i.e. larger or much larger than 1 m².

The first panel and therewith the inductive power transmitter may have any shape, but preferably is elongate and more preferably is also rectangular. It preferably has a length larger than 0.2 meter, or larger than 0.5 meter. Even more preferable is a length larger than 1 meter. The width of a first panel may be any dimension as long as its electrical components can be housed. They could have a width of 0.1 meter or larger such as for example 0.5 meter or larger.

The system as described herein before is intended to be mounted to an object that under normal use conditions is exposed to fouling. This in general means that also the system will be exposed to such conditions at least partially.

In a further aspect of the invention there is thus provided an object exposed to fouling conditions when in normal use, the object comprising an antifouling system as described herein before wherein the inductive power emitter and the plurality of inductive power receivers are mounted on the object in a fixed configuration with respect to each other thereby to provide the inductive coupling. Fixed configuration means that during use of the object the parts of the system are not displaceable. This does not mean that they cannot be removed from the object such as for example would occur during repair or replacement of parts of the system. Fixation can be done in many ways such as for example with screws, clamps or gluing of any kind.

Each one of the plurality of antifouling devices preferably comprises a UV light source for providing UV light as the antifouling radiation. The UV light works on DNA level of the microorganisms and the system based on such sources may thus work for a wide variety of antifouling.

In an embodiment of the object the antifouling system comprises
  a first panel including the inductive power emitter (10) and
  a plurality of second panels, separate from the first panel, each second panel comprising at least one of the plurality of inductive power receivers (20) and at least one of the plurality of antifouling devices,
  wherein the first panel and the plurality of second panels are mounted to the object such that different ones of the plurality of second panels are mounted at least partially to different areas of the object. The modularity of the system allows covering of the area of the object to which the system is mounted such that first and second panels are fixed to the object next to each other to cover a large area while power can be efficiently provided by a first panel to multiple second panels. The first panels preferably have an elongate shape for this purpose where second panels extend laterally from the elongate shape along the length direction to form a scheme such as herring bone.

In an embodiment the object is for partial or complete submersion in water when in normal use and wherein each one of the plurality of second panels includes one or more water resistant materials by which any of the plurality of inductive power receivers and any of the plurality of the antifouling devices present within that particular second panel are encapsulated for protecting them against water. The object preferably is one that during use is exposed to water and especially sea water. Such objects include for example buildings such as sluices, oil drilling platforms, pumping stations or buoys and vessels such as ships. A marine object may be any object as described hereinbefore or hereinafter such as for example a vessel or ship. Preferably the object is a ship. In all cases the system is mounted to the outside surface of the object such that at least the inductive power receivers (or the second panels they are part of) are mounted to this surface. Preferably also the inductive power emitters (or the first panels they are part of) are mounted to the outside surface.

In an embodiment the object has a waterline and a part of the first panel is mounted such that it remains above the waterline when the object is in use so that a power source for providing power to the inductive power emitter can be connected to the inductive power transmitter via a galvanic connection disposed above the waterline. The power source may be configured to provide the power to the inductive power emitter via a galvanic connection disposed above the waterline of the marine object. The inductive power emitter, preferably in the form of a strip as discussed above, may extend to above the waterline so that a galvanic contact may be made to the power source at a location outside the water, and the system can be fully enclosed and encapsulated below the waterline when it comes to the power provision of the load.

Thus the object comprises a surface and the antifouling system is mounted over the surface.

The object may have a coating material as defined herein above applied to its surface and between its surface and the antifouling system. This is advantageous for objects made of conductive materials near the surface such as ships with a metal hull or other constructions as defined herein that have metal parts near the surface to which the system is applied.

The invention also provides a method of mounting an antifouling system as disclosed to an object. Any of the features of the antifouling system and/or object may be used to define such method of mounting. For example there may be a method of mounting wherein at least part of the system and in particular an inductive power emitter is mounted above the waterline of an object. In an embodiment there may be applied a ferrite material and/or coating material with permittivity higher than 20 between the object and at least the inductive power transmitter.

These and other aspects of the invention will be apparent from and elucidated with reference to the embodiment(s) described hereinafter.

BRIEF DESCRIPTION OF THE DRAWINGS

For a better understanding of the invention, and to show more clearly how it may be carried into effect, reference will now be made, by way of example only, to the accompanying schematic drawings, in which.

DETAILED DESCRIPTION OF THE EMBODIMENTS

Figure 1:
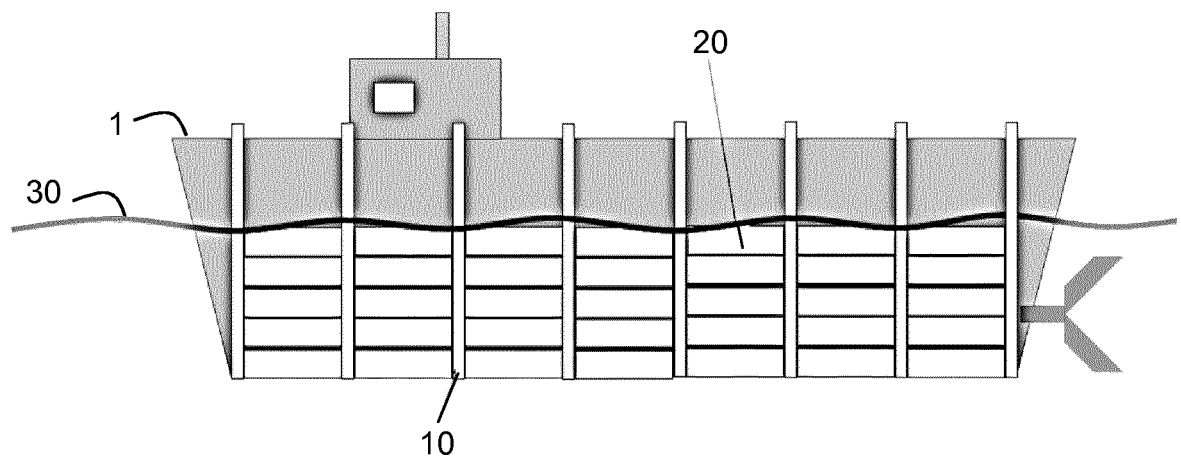
FIG. 1 shows an antifouling system of the invention applied to a ship for protecting the surface of the ship in contact with water, i.e. the hull surface.

Examples of the antifouling system as defined by the claims will be described with reference to the Figures.

It should be understood that the detailed description and specific examples, while indicating exemplary embodiments of the apparatus, systems and methods, are intended for purposes of illustration only and are not intended to limit the scope of the invention. These and other features, aspects, and advantages of the apparatus, systems and methods of the present invention will become better understood from the following description, appended claims, and accompanying drawings. It should be understood that the Figures are merely schematic and are not drawn to scale. It should also be understood that the same reference numerals are used throughout the Figures to indicate the same or similar parts.

FIG. 1 shows such an antifouling system mounted to an object in the form of a ship 1. The system is for protecting the object against fouling when the ship is used. This means that the system is at least capable of reducing fouling compared to a ship without the system. The surface in this case is the outside surface of the ship's hull parts of which below the waterline 30 of the ship may become submerged in water upon use of the ship and therewith are exposed to fouling.

In general, the waterline is the line where the surface of the object, such as for example the hull of a ship, meets the surface of the water when the object is in normal use.

The antifouling system comprises a set of (plurality of) first panels 10 each of which includes (or in the simplest embodiment is) an inductive power emitter. The first panels (and therewith the power transmitters) in this case have an elongate rectangular shape with a length longer than the width. They are mounted over the surface such that their length direction makes a non-zero angle with regard to a waterline 30 of the ship. In the Figure this angle is about 90 degrees so that the first panels extend in a vertical direction over the height of the ship. They are spatially distributed along the length direction (parallel to the waterline of the ship) of the ship.

The inductive power emitters and thus also the panels include power transmission lines such as power feed lines and power return lines. They run at least partly from one of the distal ends of the panels to the other distal ends of the panel. At the upper distal ends of the panels 10, which in this case is above the waterline 30, the power transmission lines are connected to one or more sources of electric power (not shown). Such sources may be generators of any kind or batteries etc.

The inductive power emitters each comprise one or more sets of inductive emitter elements with which electrical power can be transmitted via magnetic induction. In this case these inductive emitter elements take the form of power emitter coils each having 1 to 5 windings. However, others may be used.

In general inductive emitter elements and inductive receiver elements are meant to include any conductive element capable of carrying an alternating current so as to generate a magnetic field or capture a magnetic field by which energy may be transmitted. The coupling between two wires can be increased by winding such conductors into coils and placing them close together on a common axis, so the magnetic field of one coil passes through the other coil. Coupling can also be increased by a magnetic core of a ferromagnetic material like iron or ferrite in the coils, which increases the magnetic flux. The two coils may be physically contained in a single unit, as in the primary and secondary windings of a transformer, or may be separated. A set of primary windings can have one or more windings of wire. A set of primary windings is referred to as a power emitter coil in this document. Thus the inductive power emitter includes one or more power emitter coils.

The antifouling system further includes a set (a plurality) of second panels 20, which may be called antifouling panels. They are mounted over the surface in a spatially distributed way so that each one covers a different area of the surface of the hull of the ship. In this case all of them are mounted below the waterline 30, but there may also be some of them mounted above the waterline to account for waves when the object is used. The panels 20 in this case have an elongated rectangular shape with a length direction parallel to the waterline and a width direction perpendicular to that. They are mounted to the surface such that different panels cover at least partially different areas of the surface. In this case they do not overlap with each other at all. They have a first panel surface facing the ship with which they are attached to the ships surface and opposed to that have a second panel surface that faces the water.

These second panels each comprise at least one inductive power receiver for receiving power from one or more of the first panels 10 with which they are associated. Each of the panels 20 comprises a plurality of UV light sources for providing antifouling light by driving them with power received by the one or more inductive power receivers and transmitted by one or more of the inductive power emitters with which a panel 20 is associated. The antifouling light in this example is directed at least towards the panel surface facing the water so that at this surface, which during use of the ship is exposed to fouling, fouling may be reduced or prevented. The light sources are arranged in a light source arrangement so that they are spatially distributed over the area of a panel 20 covering part of the surface of the ship. With such an antifouling system the surface of the ship is in effect at least partly made up of the surface of the panels 20. Since the latter are protected from fouling the ship's hull surface is indirectly also protected. It is noted that the panels and sources may be configured such that the antifouling light is also provided to the ship surface for example by exiting the panels 20 at their surface facing the ship's hull surface. Thus, the light is then provided such that the surface of the ship a panel is applied to, and/or the surface of a second panel exposed to fouling (since it is now this panel surface that is exposed to water) are illuminated to reduce or prevent fouling.

Further details of how such an antifouling panel 20 can be designed and what light sources can be used to provide antifouling light are known in the art and for example described in WO 2014/188347. Therein are disclosed methods and systems for preventing biofouling in which all of a surface, or a significant amount of a surface, to be kept clean from fouling (e.g. the hull of a ship) is covered with a panel having a layer that emits germicidal light, in particular UV light such as UV C light. It is well-known that most micro-organisms are killed, rendered inactive or unable to reproduce with sufficient UV light. Thus, the light sources can be for providing Ultraviolet (UV) antifouling light. UV light is that part of electromagnetic light bounded by the lower wavelength extreme of the visible spectrum and the X-ray radiation band. The spectral range of UV light is by definition between 100 and 400 nm and is invisible to human eyes. Using the CIE classification the UV spectrum is subdivided into three bands:

UVA (long-wave) from 315 to 400 nm
UVB (medium-wave) from 280 to 315 nm
UVC (short-wave) from 100 to 280 nm Various light sources for generating UV are known, such as low-pressure mercury discharge lamps, medium pressure mercury discharge lamps and dielectric barrier discharge lamps. A preferred option, for example as proposed in WO 2014/188347 is low cost, lower power UV LEDs. LEDs can generally be included in smaller packages and consume less power than other types of light sources. LEDs can be manufactured to emit (UV) light of various desired wavelengths and their operating parameters, most notably the output power, can be controlled to a high degree. A suitable germicidal dose can easily be achieved with existing UV LEDs.

The inductive power receivers of the panels 20 each include one or more inductive receiver elements for receiving power from the coils of the inductive power emitters. In this case such inductive receiver elements take the form of power receiver coils with a number of windings for example in between 1 and 5 windings per coil. These power receiver coils are so located in the panels 20 that they are aligned with one or more of the power emitter coils of one or more of the first panels so that power may be transmitted inductively between them. Thus a power emitter coil may be seen as one side of a transformer while an aligned power receiver coil then forms the other side of the transformer. Or, in different wording, a pair of aligned primary and power receiver coils may form a transformer for power transfer.

The system of FIG. 1 is advantageous as it provides a modular system including of one or more panels 10 and a plurality of (antifouling) panels 20 with which the surface of a ship can be covered for a multitude of ships surface shapes and sizes. At the same time efficient and reliable power transfer may be provided wirelessly from a quasi-central power provision panel to the plurality of antifouling panels associated with such power provision panel. The system and power provision setup preserves or allows the modular setup and at the same time prevents or reduces effects of corrosion and consequential possible electrical short-circuiting by open electrical connections between panels. The modularity also provides the required robustness of the system as each panel 20 is powered in a parallel connectivity scheme to a power provision panel. Furthermore, the design and setup of the system allows the power panels 10 to extend above the waterline so that the quasi central power panels 10 may be connected to a power source via high current galvanic connections above the waterline.

In the example shown, the surface 18 of the ship is essentially fully covered by the antifouling panels at least below the waterline. The antifouling panels do not overlap with each other, but neighboring ones may overlap if necessary. In this case the panels are mounted to the surface such that water cannot be present between the panels and the surface of the ship. To this end they are glued with water resistant glue to the surface. Thus, the surface 18 is directly protected by the panels while the surface of the panels now exposed to the fouling are protected because of the antifouling radiation being provided to that surface. Thus, the antifouling radiation provided by the panels aims to prevent the formation of fouling organisms on the surface of the panels exposed to the fouling. This is still to be understood as forming a system for protecting the hull surface against biofouling (in that without the antifouling system, the hull surface will suffer from biofouling). Alternatively or additionally, there may be panels mounted such that water can reach the surface of the ship between that surface and the panel. In such cases the panels may be configured to provide the antifouling radiation also the ship surface and the panel surface facing the ship surface.

As will be clear from the description below, there may be multiple coils connected to a power transmission line. Many configurations of combining power emitter coils and power receiver coils can then be used each having its specific advantages. For example there may be one power emitter coil per panel or there may be multiple power emitter coils per panel. In each case each panel can have one or multiple power receiver coils to be aligned with the power emitter coils available at its location near the panel 10.

Figure 2:
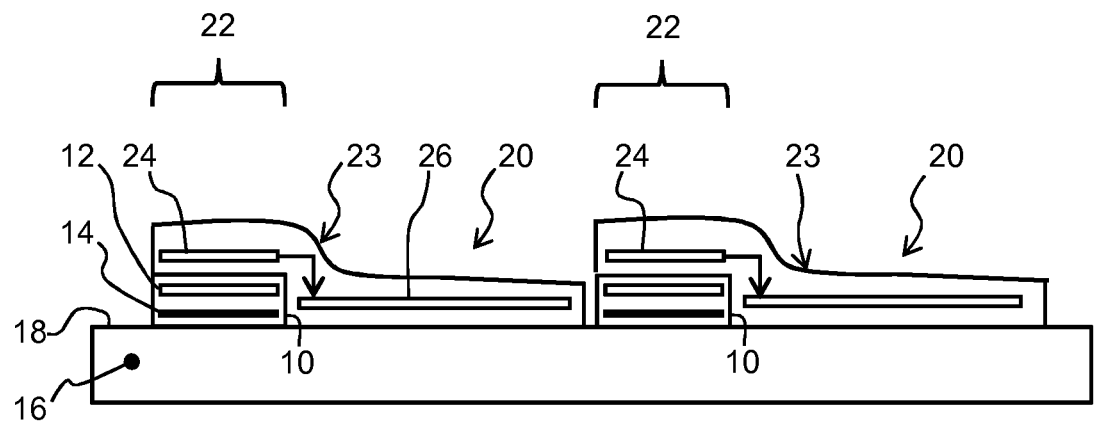
FIG. 2 shows a cross section (in a horizontal plane) of the system of FIG. 1 through the inductive power emitters, panels and part of the ship's surface.

FIG. 2 shows a cross section (in a horizontal plane) through a part of the ships' hull 16 and part of the system including two of the first panels 10 and two of the second panels 20. The surface 18 of the hull is the surface to be protected from fouling and to this end the first panels 10 and the second panels 20 are mounted against this surface 18. As indicated hereinabove, this means that the surfaces 23 of the panels 20 now effectively have become the surface exposed to antifouling. Water between the system and surface is ignored for now as in this example the panels 20 are attached to the surface in a substantially watertight fashion.

The first panels 10 each have an inductive power emitter 10 of which in turn each comprises at least one power emitter coil 12 the windings of which extend in a plane vertical to the plane of drawing. The power transmission lines of the inductive power emitters in panels 10 to which the power emitter coils 12 are connected are not drawn in the Figure but in this case would run vertical to the plane of drawing.

Each of the panels 20 comprises an inductive power receiver 20 of which each one comprises a power receiver coil the windings of which also extend in a plane vertical to the plane of drawing. The power receiver coils are located in edge regions 22 of the panels 20 and the first and second panels are mounted to the surface such that the edge regions 22 of second parts 20 overlap with the second parts 10 so that power emitter coils 12 overlap with power receiver coils 24. This may give a good inductive power transfer between the first and power receiver coils and therewith between power transmitter and receiver.

In this case counted from the surface of the ship, the panels 20 are overlapping over the panels 10 in the edge regions. This may also be the other way around.

The panels 20 each have one or more light sources arranged in a light source arrangement 26 so arranged as to provide antifouling light at least to the surfaces 23. The wirelessly transmitted power by the panels 10 is used by the panels 20 to power the light sources in the arrangements 26.

In the current example the ships' hull is made of steel in which Eddy currents may occur at the locations of coils during power transfer. Such Eddy currents may reduce efficiency of power transfer. To reduce or prevent such loss of efficiency, the second panels 10 have a ferrite material in the form of a ferrite sheet 14 between the power emitter coil and the metal of the hull 16 of the ship. The ferrite material reduces or even prevents Eddy currents in the metal of the ship's hull 16 thereby increasing the efficiency of energy transfer. High permittivity materials could also be used for this purpose. It will be clear that when Eddy currents do not significantly occur, such ferrite material or other solutions are not needed. For example when the hull is made of non-conducting material such as plastic or wood.

The power emitter coils may be formed on or within a printed circuit board (PCB) which in turn may be part of the inductive power emitter and/or power transmission lines. Likewise, the power receiver coils may be formed on or within a PCB of an inductive power receiver. The light source arrangement may also be formed on a PCB, which may be separate to, or the same as, the PCB of the power receiver coils. The PCBs are not shown in the figures, to keep the shown structure simple. The PCBs are thus also parts of the respective panels.

There may be a single shared flexible PCB in a panel for example having the coils and the light sources as well as other parts of the electronic power provision circuit within a panel. Such flexible panel is then capable to adapt to the contour of the surface they are mounted on. Instead, there may be separate PCBs in the panel and an electrical connection between them.

Electrical circuits in the form of PCBs are convenient, but need not be used perse. Other ways of making the electrical circuits can be used as well.

Parts of the panel circuits may be made using PCB while other parts may be made with different methods. For example, the light source arrangement may be formed as a wire grid structure instead of a PCB having distributed light sources. This reduces the PCB area since a PCB is needed only for the power receiver coils. In further variants, the entire panel circuits are devoid of PCB and made with other techniques.

The power emitter coils of the inductive power emitters 10 may for example be supplied with a 100 kHz to 150 kHz AC supply (sinewave) during operation of the system. To compensate for a capacitive leakage current to the hull 16 at the position of the power transmission lines, these (and therewith the inductive power emitter) may further be provided with a capacitor to implement a low pass filter. This is for example of interest if high efficiency switched amplifiers are used to generate the AC supply. In such a case, the low pass filter is used to filter out residual higher frequency harmonics of the amplifiers. An alternative is to use a resonant circuit to generate the AC supply. For example, each power transmission line (inductive power emitter) may comprise a resonant circuit, based on a capacitive resonant circuit, with a resonance in the range 60 kHz to 90 kHz.

Generally, the frequency of operation (resonant or driven) may be in the range 50 kHz to 1 MHz, for example 50 kHz to 200 kHz, for example 60 kHz to 90 kHz.

Figure 3:
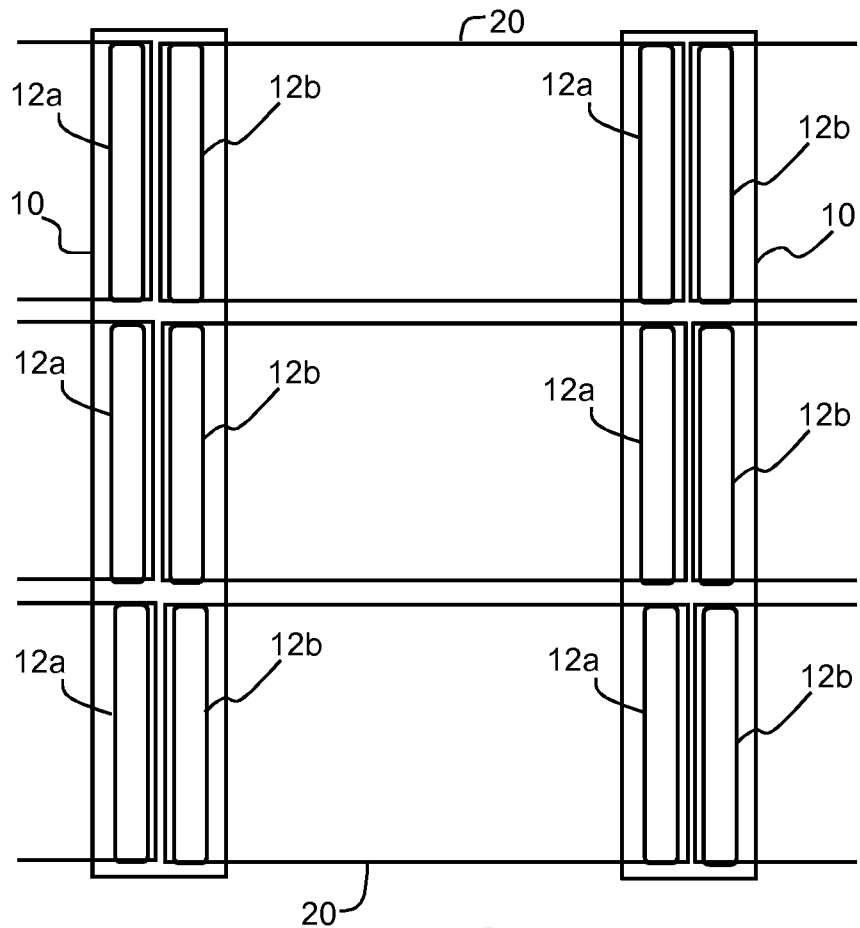
FIG. 3 shows the coil arrangements in more detail.

FIG. 3 shows exemplifying arrangements of panels and their overlap.

The example of FIG. 2 has the panels 10 overlapping an associated panel 10 at one lateral edge. In FIG. 3, the panels 20 overlap panels 10 at both lateral edges, and each panel 10 has pairs of power emitter coils, e.g. horizontally neighboring 12*a* and 12*b*, arranged along its length (length is vertical in the plane of the drawing). One coil of a pair, e.g. 12*a*, is for powering a second panel 20 to one side and the other coil of the pair, e.g. 12*b*, is for powering a second panel 20 to the other side. In this way, each second panel 20 is supplied by power from two sides and thus from two different first panels. This principle may be extended to more than two sides when a grid of first panels is used instead of a set of more or less parallel extending first panels 10. This may make the system more redundant against damage of first panels 10 and or of second panels 20.

All power emitter coils of the first panels 10 can have the same phase, which contributes to electric redundancy of the system. The light source arrangements 26 can still function in their entirety if a power transmission line in the inductive power emitter of a first panel is broken. In that respect, the inductive power emitters and the power transmission lines may be designed to deliver electric power at an increased level of two times a normal level.

Thus, there may be one coil assembly (i.e. power emitter coil and power receiver coil) per panel (FIG. 2) or two coil assemblies per panel (FIG. 3). There may even be more than two with assemblies on yet further sides of panels (not shown).

The first panel and the second panels of the antifouling system comprise encapsulation material for protecting parts and especially electrical parts of the system involved in powering of the system. That is, all parts of the system that are normally exposed to the water when the system is in use have such encapsulation. Thus, in the example described herein above, a panel includes such encapsulation which encapsulates its electrical circuits responsible for receiving power and driving of the light sources. The encapsulation in this case is for all of the electrical parts including for example the coils, power conduction lines and PCBs. An exception could possibly be a sensor device in a panel or at least those parts of the sensor device that need galvanic contact with water to be able to provide a sensory function. Preferably however in the system sensors that operate on a sensory principle that does not require galvanic electrical contact are employed (e.g. capacitive or other). The encapsulation prevents or at least reduces water reaching these electrical power provision parts and driving circuits of the system. The encapsulation may have the form of material in which all electrical components are embedded. The material may be called a water tight material having at least a reduced water penetration characteristic. The panel may thus be called a water tight panel. Suitable materials for this purpose will be described herein below but one type is based on silicone polymers.

The panels 10 of the system also comprise encapsulation material to encapsulate the inductive power emitter including coils, power transmission lines and PCB's or other. However, there may be a galvanic connector for connection to a power source that is to the outside of a panel 10. Such connector or connection is then preferably at a location of such panel 10 that is positioned on a surface part that is not submerged in water during use of the ship thus for example above the waterline.

With such encapsulated modular system there are no galvanic electrical contacts for providing power from the strip to a panel or vice versa (if needed) or between panels. Hence while the encapsulation may reduce or prevent corrosion, power can be conveniently provided to the different watertight parts of the modular system. At the same time the systems modularity is preserved to provide an advantageous setup for efficient coverage of surface areas to be protected such as the ship's hull.

As shown in for example FIG. 1, the antifouling system has multiple first panels 10 and panels 20 for covering a surface of the ship. For example there may be more than 2, more than 5 more than 10 more than 20 or even more than 50 panels 20 coupled to an inductive power emitter of a first panel 10. In a simplest arrangement to cover a surface there is only one first panel 10 and a plurality of second panels 20 each associated with the single first panel 10 to be powered by that panel. However in the example of FIG. 1 there are multiple first panels 10 and a plurality of second panels 20 is coupled to each of these multiple first panels 10.

With such a modular system application of the system to a surface may be facilitated or more convenient in relation to a single element system. Also irregular and or non-flat shaped surfaces such as curved surfaces (as may happen with a ship's hull) can be more easily covered. The freedom in alignment of coils of a transformer (alignment of primary and power receiver coils) will be beneficial in this respect. It is noted however that such freedom is needed only during application of the system to the surface or object as once applied it is to be retained in a fixed position or configuration (apart from situations of repair). The number of second panels 20 per first panel 10 and/or number of panels 10 and 29 per surface area may be chosen as desired based on the one hand on shape, area and dimensions of panels and on the other hand on the areas and dimensions of the surface to be covered. With the system a flexible design option for the antifouling system can be realized.

In the example shown, the first panels 10 and thus the inductive power emitters 10 and the included power transmission lines extend in a substantially vertical orientation along the side of the ship. The second panels 20 are arranged successively along the length direction of such a first panel 10 and extend substantially laterally with respect to this length direction. However, any suitable arrangement of panels is possible. The first panels may be parallel to each other, but this need not be the case. They may make an angle of less than 90 degrees with the water line of the ship. They may even be parallel to the waterline of the ship. They do not need to be straight, but may have one or more curves or bends. This may be advantages for application to surfaces that are not inherently flat. In such case the panels may also have a shape adapted to fulfill this purpose of coverage of inherently non-flat surfaces. The panels 10 may for example cover welding seams and/or other surface irregularities of the ship's hull. In all cases it may be advantages to have a first panel extend to above the water line to allow a contact to a general power source such as the ships generators to be located in a non-submerged area when the ship is in use.

Figure 4:
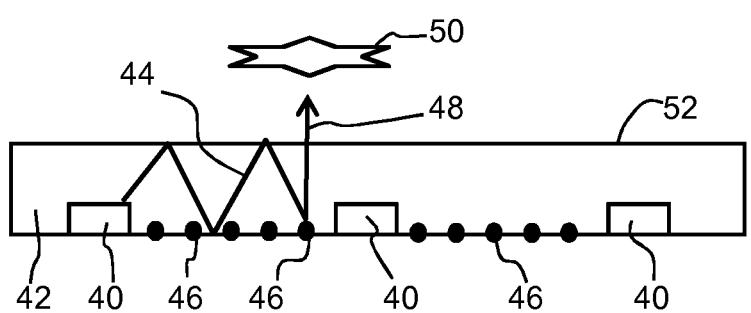
FIG. 4 shows an example of the structure of the panel.

FIG. 4 shows a cross section of an example of the structure of the second panel 20 having a plurality of light sources 40 which in this example are side-emitting UV-C LEDs, wherein the light is emitted primarily from a side of the LED, and more or less parallel to the surface 52. Other configurations may work too. The light sources 40 are encapsulated and in this case, although not needed per se, embedded in an optical medium or material 42 to guide at least part of the light 44 emitted from the light sources 40 via total internal reflection through the optical medium or material. The light is guided at least towards the surface 52 of the panels exposed to water but may also be guided to other surfaces or parts such as the surface opposing the surface 52. This medium or material may be and preferably is the same as the water tight encapsulation material mentioned herein before. Again suitable materials will be described herein below.

Optical structures 46 are provided to disrupt the total internal reflection and scatter light, and then guide the scattered light 48 out of the optical medium 42 towards a target for the light, which is an area where a biofouling organism is present. These optical structures are not needed per se.

A biofouling organism on the surface 52 will directly receive the scattered light 48 before it enters the water so that the light may exerts its antifouling effect by disrupting important biochemical growth mechanisms of the organisms as described in the art. Especially UV-C light has been found to be effective in this respect.

The optical medium is relatively thin so that the panel may be considered to be a two-dimensional structure having a thickness of for example less than 3 cm or preferably less than 2 cm or even less than 1 cm. The optical structures 46 to scatter light may be spread in one or more portions of the optical medium material, possibly throughout all of it, and the light output may be generally homogeneous or else localized.

Internal scattering centers with different structural properties may be combined to provide optical and well as structural characteristics, such as resistance to wear and/or impact. Suitable scatterers comprise opaque objects but largely translucent objects may be used as well, e.g. small air bubbles, glass and/or silica; a requirement is merely that a change in refractive index occurs for the wavelength(s) used.

The principle of light guiding and spreading light over a surface is well-known and widely applied in various fields. Here, the principle is applied to UV light for the purpose of antifouling.

To maintain the conditions for total internal reflection, the index of refraction of the light guiding material should be higher than that of the surrounding medium. However, the use of (partly) reflecting coatings on the light guide and/or the use of the reflective properties of the protected surface, e.g. the hull of a ship, itself can also be used to establish the conditions for guiding the light through the optical medium.

In the example above, the panels form a new surface over the surface to be protected (the surface of the object which in this case is the outer surface of the hull of a ship), and light is directed outwardly from the surface to be protected. However, an alternative is for the panel to be spaced over the surface to be protected and to direct light back towards the surface to be protected. A combination of the two is also possible in that the panels may direct their emitted light to its opposing surfaces one of which will face the water and one of which will face the hull surface.

A small air gap may then be introduced between the light source arrangement of the panel and the surface to be protected. UV light may travel better, with less absorption, in air than in an optical medium, even when this optical medium is designed as a light guiding material.

As most materials have a (very) limited transmittance for UV light, care has to be taken in the design of the optical medium. As a result, a relatively fine pitch of low power LEDs can be chosen, to minimize the distance light has to travel through the optical medium.

In one example, the optical medium 42 comprises a silicone based material, and one which is designed to have good UV-C transparency.

A solid encapsulation may be used in which case parts of the panel are embedded in the encapsulation material, as shown in FIG. 4. However, a hollow structure may instead be used, such as a silicone mat with spacers that keep it a small distance away from the protected surface. This creates air channels, through which the UV light can propagate with higher efficiency. Use of gas filled channels provided by such structures allows distributing the UV light over significant distances in an optical medium of material that would otherwise absorb the UV light too strongly to be useful for antifouling. Similarly, separate pockets may be formed.

Figure 5:
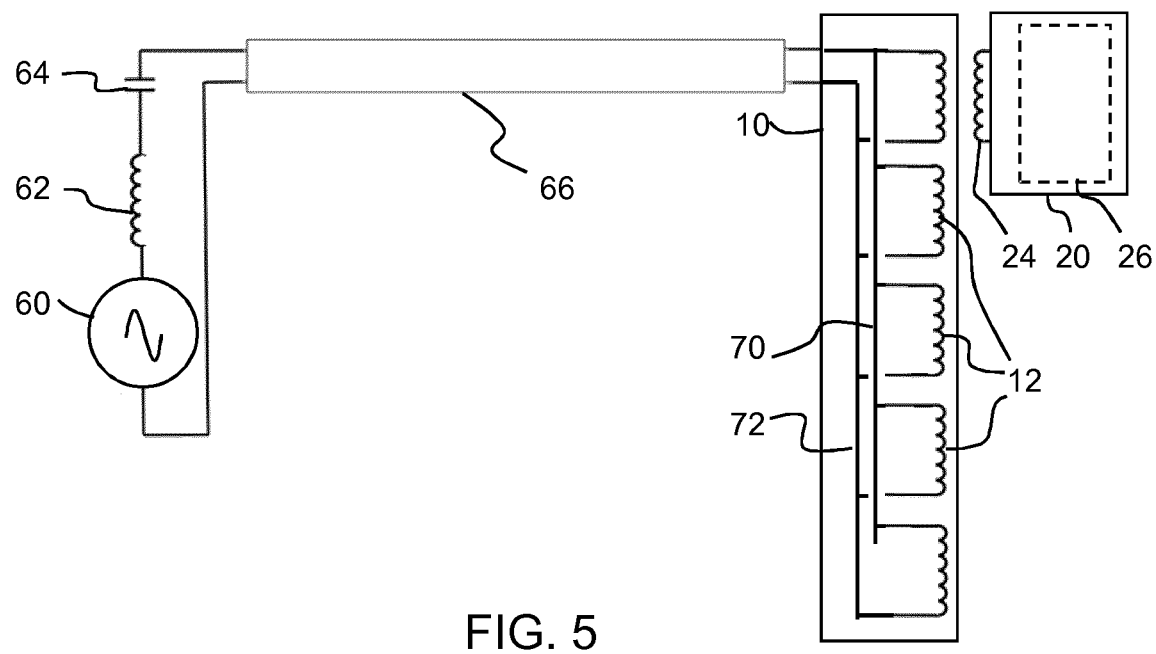
FIG. 5 shows one possible electrical configuration of the primary and power receiver coils.

FIG. 5 shows an electrical configuration of an antifouling system, for example the one of the system of FIG. 1.

The system includes a power source for delivering power to the inductive power emitter. The power source comprises an AC driver 60, a tuning coil 62 and a tuning capacitor 64. The power source connects to the inductive power emitter 10 of the system by a cable 66. In particular the cable leads connect to the power feed line 70 and the power return line 72 of the power transmission line. This connection between the power transmitters and the power source can now be made galvanic and above the waterline of a ship where such galvanic connections are less prone to corrosion in watery conditions. In the arrangement shown, the inductive power emitter 10 comprises a set of power emitter coils 12 (5 are shown) arranged physically in a line along the power transmission line, but electrically connected in parallel.

The panel (only one of which is shown for clarity) includes the power receiver coil 24, aligned with and therefore magnetically coupled to one of (the top shown one) the power emitter coils 12. The coils are shown next to each other in the drawing and although this may in practice be a real situation, preferably the coils are designed and arranged such that they are on top of each other as described herein before.

For long power transmission lines for driving many second panels, such as e.g. more than 10, the power transmission line is preferably at least partly balanced and more preferably fully balanced. A balanced transmission line may be a transmission line consisting of two conductors of the same type, each of which have equal impedances along their lengths and equal impedances to ground and to other circuits. The power transmission line then behaves as a balanced transmission line and can then be driven with a balanced driver such as an H-bridge. This has advantages for electromagnetic compatibility (EMC) and for the driver, for example because both PCB leads, i.e both the power feed line lead and power return line lead of the power transmission line, can see the same impedance (e.g. same capacitance) to the ship's hull and to the water. In a balanced situation the EMC stray fields, which deteriorate the emission behavior at the driving frequency, will balance out. This improves antenna efficiency.

The balanced power transmission line can be made in the form of a twin lead with two conductor strips held at a precise constant mutual distance along the transmission line and with an insulator in between the conductor strips. This allows use of a single metal layer PCB and may provide a thin solution for the system. Alternatively, or additionally, the power transmission line can be a twin lead including two metal conductors on top of each other with an insulator layer in between. Again the distance between them is kept at a constant value along the conductors lengths. In such case the power feed line may be on top of the power return line of a power transmission line or vice versa with reference to the systems' surface attached to the object surface when in use.

A two layer PCB design may also be used to enable cross overs in conductors to be formed for example close to the coils as there will be windings connected to the power transmission line.

Figure 6:
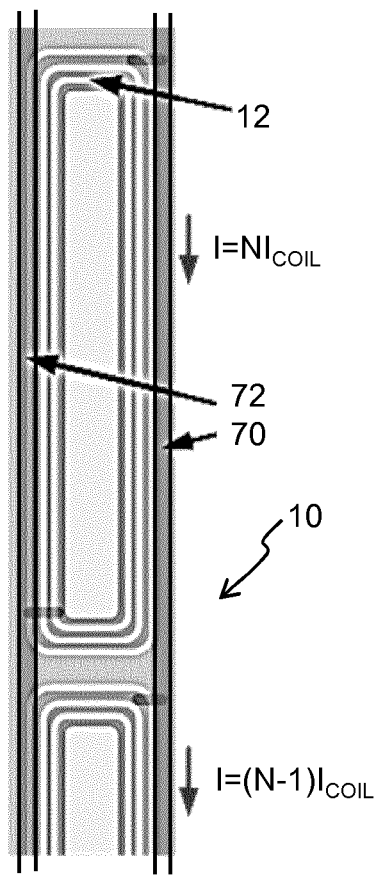
FIG. 6 shows a first way of arranging power emitter coils and power transmission line within an inductive power emitter.

FIG. 6 is shows an arrangement in which the power feed line 70 is down one side of the power emitter coils and the power return line 72 is down an opposite side of the power emitter coils. Less crossovers may be needed for connections. However, the magnetic field in the coils is now dependent on the current through the power power power feed lines as the current through a power feed line and a power return line both generate a magnetic field which fields add up at the inner coil areas, i.e. they add to the magnetic flux of the coils. As current passes along the power feed line, current is tapped off by each coil in turn (thus coil C1 tapps of before coil C2) and, as a result, the total current flowing thus depends on the position along the power feed line. For example, at one location, the current is $NI_{COIL}$ where $I_{COIL}$ is the current drawn by each power emitter coil, and there are N coils still to be supplied with current. Past the next coil, the current is $(N-1)\ I_{COIL}$. Thus, the current generating a magnetic field in a particular coil is a function of position of the coil. As a result, the power transmission within a particular coil is a function of position of that particular coil along the inductive power emitter (or panel it is part of). This means the different power receiver coils driven by different power emitter coils may be driven to different voltages or currents. In some cases this is an advantage but in others it may be a disadvantage.

Figure 7:
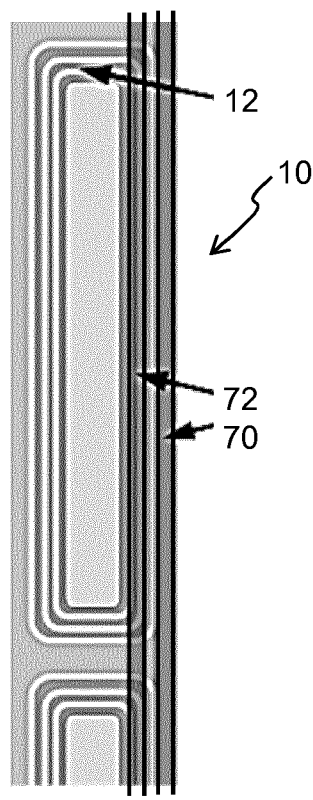
FIG. 7 shows a second way of arranging power emitter coils and power transmission line within an inductive power emitter.

FIG. 7 shows a first approach to address this disadvantage. The inductive power emitter 10 again comprises a plurality of power emitter coils 12 (C1 and C2 are shown) electrically in parallel positioned physically series along the length of the power transmission line. The power feed line 70 extends from one end of the feeding line to the plurality of power emitter coils and the power return line 72 extends from the plurality of power emitter coils to the one end of the feeding line. The power feed line and the power return line in this case are side by side and in this case at one side of a power emitter coil. In this case even to the same side of multiple power emitter coils, but this is not necessary per se. In this way, the magnetic fields caused by the power feed line and power return line (which are of different strengths along their length as a result of the tapping off of current between coils) are substantially cancelled at the power emitter coil location. Consequently a more uniform magnetic field strength is achieved within the power emitter coils.

The arrangement may for example be driven with a voltage controlled driver to ensure the voltage does not exceed safety levels.

Figure 8:
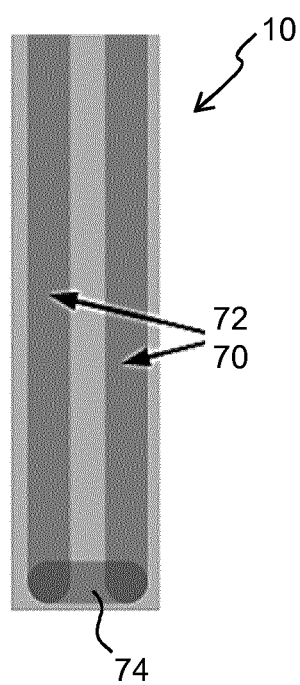
FIG. 8 shows a third way of arranging a power emitter coil using power feed line and power return line of an inductive power emitter.

FIG. 8 shows a second approach to address the non-uniform power transmission of FIG. 6. The inductive power emitter 10 comprises a single coil extending along the length of the transmitter or panel. It is as if the coil also performs the function of feeding line. The single coil is then for magnetic coupling to the power receiver coils of the plurality of inductive power receiver panels to be associated or driven by this inductive power emitter. Thus, a single power emitter coil, formed of a power feed line 70 and power return line 72 with a connecting bridge 74 at the end of the feeding line is used to magnetically couple to a set of power receiver coils. In this way, the magnetic field coupling to each power receiver coil is the same or close to the same.

The use of a single coil relaxes the vertical and/or angular accuracy with which the power receiver coils need to be aligned with the power emitter coils. The arrangement may for example be driven with a voltage current controlled driver or current controlled driver. The use of one power emitter coil only means the voltage is more easily controlled so that current driving is also an option. The power emitter coil again may have multiple windings such as 1 to 5.

Figure 9:
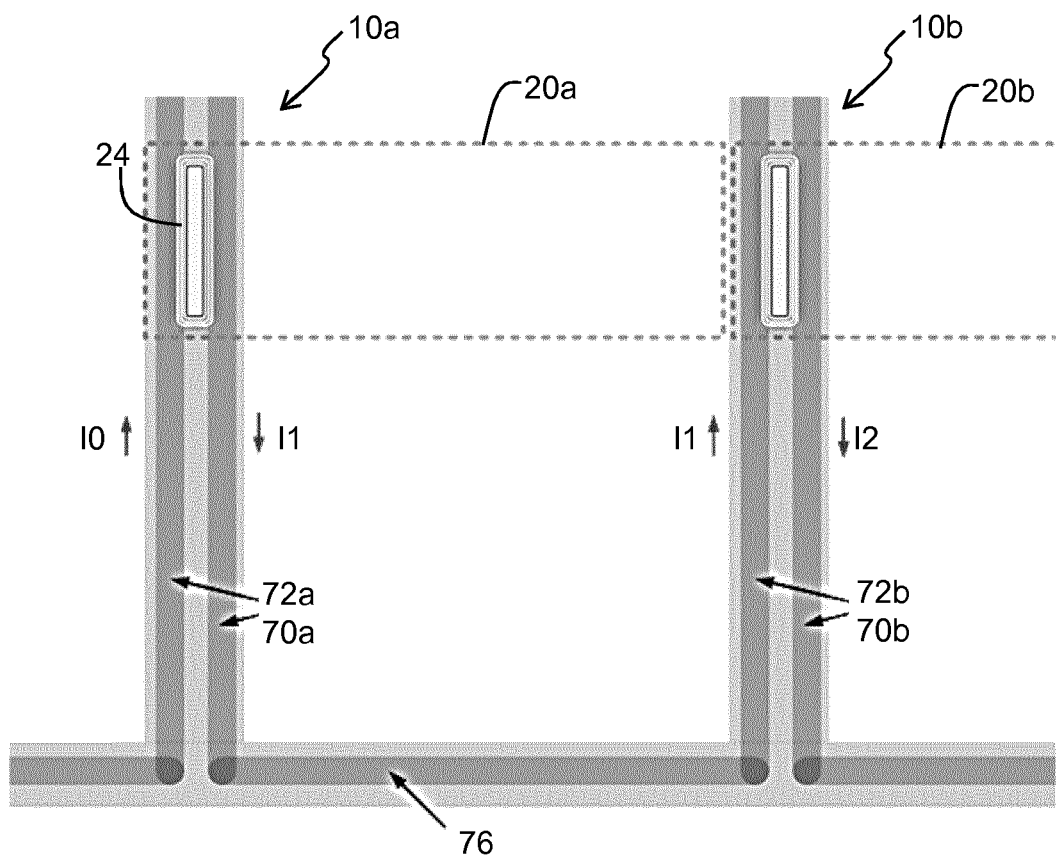
FIG. 9 shows a way of arranging a power return line of one inductive power emitter and a power feed line of another inductive power emitter such that they together form a inductive emitter element.

FIG. 9 shows a third approach to address the non-uniform driving disadvantage indicated herein before in relation to the example of FIG. 6. In this third approach the inductive power emitter comprises a set of conductive elements in the form of power transmission lines 10a, 10b. Each feeding line is associated with a respective plurality of inductive power receiver panels which each extend laterally from a respective position along the feeding line. Feeding line 10a is associated with (and provides power to) panel 20a and also other panels forming other rows (not shown). Feeding line 10b is associated with (and provides power to) panel 20b and also other panels forming other rows (not shown).

Each feeding line 10a, 10b comprises a power feed line 70a, 70b and a power return line 72a, 72b. The power power feed lines and power return lines each extend from a first end of the feeding line (the top in FIG. 9) to a second end of the feeding line (the bottom in FIG. 9). The power feed line and the power return line of any given power transmission line form parts of a conductive element capable of transferring power. After all, their neighboring parts generate magnetic fields between them that may add up.

Thus, in this implementation the individual feeding lines do not have coils. Instead, they define one half (e.g. the feed part) of one power emitter coil and one half (e.g. the return part) of another power emitter coil. There is again one quasi power emitter coil (no actual windings are formed) which extends over the full length of the pair of feeding lines.

Connecting members 76 are provided between the second ends of adjacent feeding lines, to connect the power feed line e.g. 70a of one feeding line 10a with the power return line e.g. 72b of an adjacent feeding line 10b to one side (the right in FIG. 9) and to connect the power return line 72a of said one feeding line 10a with the power feed line an adjacent feeding line to the other side (the left in FIG. 9, not shown). The connecting members are away from the panels. The leakage inductance caused by the connecting members 76 can be tuned with a capacitor at the first (top) end of the feeding line to make the overall arrangement function as a resistive load, thereby improving efficiency by cancelling blind currents.

A first current I1 flows down power feed line 70a and back via power return line 72b. The power receiver coil 24 overlaps the pair of adjacent feed and power return lines at the location where the magnetic field of these power power feed lines add up. Thus, the current flows in large loops, but the magnetic coupling to the power receiver coils 24 is by means of the local oppositely flowing currents.

To ensure the local currents (e.g. I0 and I1) flow in opposite directions to make the magnetic fields of power power feed lines add up at the desired locations, adjacent large loops are driven out of phase with each other.

This third option arrangement may be easier to mount to a surface.

In the examples above, the second panels 20 overlap the first panel 10 in order to have power receiver coils overlap power emitter coils. This provides galvanic isolation between the power supply and the structure which is exposed to the water. The panel also protects the underlying feeding line. Instead, or in addition the first panels may be provided over the second panels. A separate electrical isolation may be provided (e.g. at the top of the feeding lines). The surface of the strips may then be susceptible to biofouling, so it should then be ensured that light reaches the surface of the feeding lines, either by transmission through the feeding lines or by reflection or waveguide transmission within the panels or by adding a light sources to the first parts.

Thus in the above examples, the inductive power emitter and the panel are both for mounting over the surface, but in either order.

Alternatively, only the panels are mounted over the surface. The strips are still applied to the object such that power emitter coils align with power receiver coils, but not to the same surface. For example, the strips are applied to the inside of the ship's hull and power is then transferred through the ship's hull. A wooden or plastic hull could work in that way. Alternatively, the hull could have holes for harboring the power emitter coils.

Figure 10:
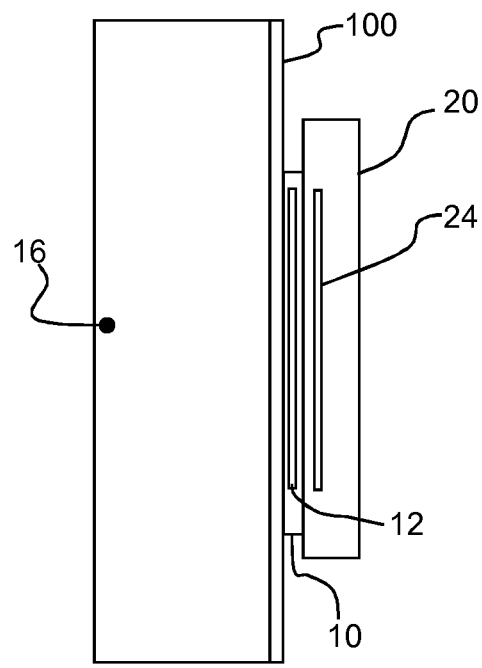
FIG. 10 shows an arrangement in which the inductive power emitter and inductive power receiver panels are provided over a high magnetic permeability paint layer.

As mentioned, some of the examples above makes use of a ferrite sheet 14 below the windings to reduce Eddy currents. An alternative shown in FIG. 10 is to provide the inductive power emitter 10 and inductive power receiver 20 over a paint material 100 on the surface. The paint material includes ferromagnetic or other high permeability particles such that it has a relative magnetic permeability greater than 20, for example greater than 100 or even greater than 200. The additional layer for preventing the eddy currents may also be omitted. For example when a ship's hull is less prone to providing such currents. This could be in case of wooden or plastic type hulls.

A high permeability paint can function as a replacement for a ferrite layer. It has good insulation properties but conducts magnetic field. Thus, it functions to shape the magnetic field but prevent induced currents in the underlying conducting layer, such as a ship's hull.

For the application of the invention to a biofouling prevention system, a typical secondary side current is 0.1 A and a typical desired secondary side voltage is around 40V. For safety, a maximum voltage of 50V rms (by way of example only) may be considered. The system is designed or operate below the maximum voltage, taking into account all the characteristics of the inductive coupling and the spreading of currents. For a given operating voltage, the required current depends on the required power. A higher voltage enables a lower current and vice versa.

The feeding lines for example make use of a PCB with thickness of less than 1 mm, for example 0.5 mm, created a molded structure thickness of around 3 mm.

The panels for example have a PCB thickness of 0.8 mm, and the total thickness with the silicone of below 5 mm, for example in the range 2 mm to 4 mm.

A panel may have many shapes such as triangular or rectangular. They may have an area of 0.5 $m^2$ or larger. Preferably they have an area of 2.5 $m^2$ or larger. The sides of such panels may be of dimensions (length and width) larger than 0.1 or 0.2 meter, preferably larger than 0.5 meter. Not all sides of a panel, or of different panels in case there are more in a system, need to have the same dimensions. The panels for example have a length (along the horizontal row direction) in the range 1 m to 5 m and a height (along the vertical column direction) in the range 50 cm to 150 cm. For example a small panel dimension may be 600 mm×1200 mm and a large panel dimension may be 1 m×4 m. An example area to be covered, e.g. one side of a ship hull, may be of the order of 100 m length by 10 m height. But this may all depend on the size of the surface to be covered and thus the size of the object.

The shapes and sizes (area) or dimensions (length, width) of the strip and panels may be any as long as suitable for use in an antifouling system to be able to protect ore even cover the surface. They shapes and sizes may be chosen according to size and shape of the surface they need to be applied to. Since the surface preferably is one of an object such as a vessel, and ship, etc., such surfaces are in general quite large, i.e. larger or much larger than 1 $m^2$.

The first panel 10 may have any shape, but preferably is elongate and more preferably is also rectangular. It preferably has a length larger than 0.2 meter, or larger than 0.5 meter. Even more preferable is a length longer than 1 meter or longer than 5 meters. The width of a first panel may be any dimension as long as its electrical components such as e.g. coils and/or power transmission lines can be housed. They could have a width wider than any one of the following values: 0.1 meter, 0.2 meter, 0.3 meter, 0.4 0.5 meter or larger.

The antifouling implementation is of interest for objects to be at least partly submerged in water, where water means any type of water known to host biofouling organisms such as river, lake or sea water. Examples of marine objects include ships and other vessels, marine stations, sea-based oil or gas installations, buoyancy devices, support structures for wind turbines at sea, structures for harvesting wave/tidal energy, sea chests, underwater tools, etc. and parts of all of these. For biofouling prevention, the system may be applied to lock doors, silo tanks in the food industry, and drinking water vessels.

The antifouling use of the invention can be applied to a wide variety of fields. Almost any object coming into contact with natural water, will over time be subject to biofouling. This can hinder e.g. water inlets of desalination plants, block pipes of pumping stations, or even cover the walls and bottom of an outdoor pool. All of these applications would benefit from the presently provided method, lighting modules and/or system, i.e. an effective thin additional surface layer, which prevents biofouling on the entire surface area.

In preferred examples, the light sources are UV LEDs as explained above. A grid of UV LEDs may be encapsulated in a liquid-tight encapsulation, of which silicone is only one example. The UV LEDs may be electrically connected in a series and/or parallel arrangement. The UV LEDs are for example packaged surface mount LEDs, in which case they already may include an optical element to distribute the light emitted from the LED package across a wide emission angle. In other embodiments, the UV LEDs may be LED dies, typically not comprising optical elements but being significantly thinner than packaged LEDs. As an example, LED dies could be picked and placed onto a surface of the optical medium The silicone material that can be used as encapsulation material and/or optical material can be selected to provide optical transmission for UV light with little loss compared to other materials. This is in particular the case for shorter wavelength light, e.g. UV light with wavelengths below 300 nm. A particularly efficient group of silicone materials is, or at least comprises, so-called methyl silicones, according to the general chemical formula $CH_3[Si(CH_3)_2O]_nSi(CH_3)_3$, with "n" indicating any suitable integral.

Silicone materials are also flexible and resilient so that they are robust, durable and capable of withstanding compression such as due to bumps, collisions etc. of objects against the surface, e.g. bumping of a ship against a quay. Furthermore, deformation due to temperature fluctuation, pounding by waves, flexion of the ship over swell etc. may be accommodated.

The encapsulation may have multiple materials that may be layered as known in the contemporary art in this new light based antifouling systems field.

At least part of light emitted by the one or more light sources may be spread in a direction having a component substantially parallel to the surface to be protected. This facilitates distributing the light over significant distances along the protected surface, or the application surface of the foil, which assists in obtaining a suitable intensity distribution of the antifouling light.

A wavelength conversion material may be comprised in the optical medium and at least part of the antifouling light may be generated by photo-exciting the wavelength conversion material with light having a first wavelength causing the wavelength conversion material to emit the antifouling light at another wavelength. The wavelength conversion material may be provided as an up-conversion phosphor, quantum dots, nonlinear media such as one or more photonic crystal fibers etc. Since absorption and/or scattering losses in the optical medium for light of different, mostly longer, wavelengths than UV light tend to be less pronounced in the optical media, it may be more energy-efficient to generate non-UV light and transmit that through the optical medium and to generate UV antifouling light at or near the desired location of use thereof (i.e. emission form the surface into the liquid environment).

One example described above makes use of side-emitting LEDs and optical scattering sites. However, light spreading arrangements may be used to create the sideways light. For example, a cone may be arranged in the optical medium and positioned opposite the light source, where the opposing cone has a surface area with a 45° angle perpendicular to the protected surface for reflecting light emitted by the light source perpendicular to said surface in a direction substantially parallel to said surface.

The LEDs may be DC driven. However, a pair of back to back parallel LEDs may be driven by an AC drive signal.

As mentioned above the LEDs are preferably mounted on a PCB, and PCB tracks (on the PCB surface or internally within layers of the PCB) form the receiver coil. However, the LED grid may instead be formed by connecting LEDs to a connection nodes of a freestanding wire structure by soldering, gluing or any other known electrical connection technique. This may be combined with a power receiver coil on a smaller PCB.

Although UV light is the preferred solution, other wavelengths are envisaged as well. Non-UV light (visible light) is also effective against biofouling. Typical micro-organisms are less sensitive to non-UV light than to UV light, but a much higher dose can be generated in the visible spectrum per unit input power to the light sources.

UV LEDs are an ideal source for thin light emitting surfaces. However, UV sources other than LEDs can also be used, such as low pressure mercury vapor lamps. The form factor of these light sources are quite different; mainly the source is much bigger. This results in different optical designs, to distribute all the light from a single source over a large area. Further, a significant contribution of light in desired wavelengths and/or wavelength combinations may be produced. Instead of using a thin layer that emits UV light outward in a direction away from the protected surface in order to avoid bio-fouling, biofouling could potentially also be removed by applying UV light from the outside in the direction of the protected surface, as explained above. The panel may instead emit antifouling light both in directions towards and away from the surface to be protected.

The antifouling system exemplified are based on providing antifouling light used for protecting a surface against biofouling while the surface is submerged in water. While this is a preferred application area where the system may have its profound advantages, the use of the system is not necessarily limited to such circumstances as submergence in water as biofouling may also occur on surfaces exposed to the atmospheric environment.

Variations to the disclosed embodiments can be understood and effected by those skilled in the art in practicing the claimed invention, from a study of the drawings, the disclosure and the appended claims. In the claims, the word "comprising" does not exclude other elements or steps, and the indefinite article "a" or "an" does not exclude a plurality. The mere fact that certain measures are recited in mutually different dependent claims does not indicate that a combination of these measures cannot be used to advantage. If the term "adapted to" is used in the claims or description, it is noted the term "adapted to" is intended to be equivalent to the term "configured to". Any reference signs in the claims should not be construed as limiting the scope.

The invention claimed is:

1. An antifouling system for reducing and/or preventing fouling of an object exposed to fouling conditions, the antifouling system comprising:
a plurality of antifouling devices for providing antifouling protection to at least part of a surface of the object that is beneath a waterline of the object in a marine environment, and/or at least part of the antifouling system;
a power transmission system comprising:
an inductive power emitter comprising at least one inductive emitter element; and
a plurality of inductive power receivers each one comprising at least one inductive receiver element;
wherein the plurality of antifouling devices is situated on the surface of the object;
wherein the inductive power emitter and the plurality of inductive power receivers are for mounting on the object in a fixed configuration with respect to each other thereby to provide an inductive coupling between each one of the at least one inductive receiver elements and the at least one inductive emitter element such that power is inductively transmitted when the power transmission system is in use; and
wherein the plurality of antifouling devices are configured to be driven using transmitted power from at least one of the plurality of inductive power receivers when the system is in use.

2. The antifouling system of claim 1, comprising:
a first panel including the inductive power emitter and
a plurality of second panels, separate from the first panel, each second panel comprising at least one of the plurality of inductive power receivers and at least one of the plurality of antifouling devices.

3. The antifouling system of claim 2,
wherein each one of the plurality of inductive power receivers are configured such that the at least one power emitter element of an inductive power receiver at least partly overlaps with the at least one power emitter element when the system is mounted to the object and
wherein each one of the plurality of second panels comprises one or more edge regions in which its at least one power receiver element is disposed.

4. The antifouling system of claim 1 wherein each one of the plurality of antifouling devices comprises a UV light source for providing UV light as antifouling radiation.

5. The antifouling system of claim 1,
wherein the one or more inductive emitter elements each comprises one or more power emitter coils,
wherein the one or more inductive receiver elements each comprises one or more power receiver coils, and
wherein the inductive power emitter and the inductive power receivers are configured such that each one of the one or more power receiver coils at least partly overlaps with at least one of the one or more power emitter coils when the system is mounted to the object.

6. The antifouling system of claim 1,
wherein the inductive power emitter comprises a power feed line and a power return line,
wherein the at least one inductive emitter elements comprises a plurality of inductive emitter elements each one electrically connected in parallel configuration to the power feed line and to the power return line and physically positioned in series with respect to each other within the inductive power emitter, and
wherein each one of the plurality of inductive emitter elements is arranged to inductively couple to at least one of the at least one inductive receiver elements of one of the plurality of inductive power receivers.

7. The antifouling system of claim 1,
wherein the inductive power emitter comprises:
at least one inductive emitter element,
a power feed line, and
a power return line, and
wherein each one of the at least one inductive emitter element comprises a section of the power feed line and a section of the power return line.

8. The antifouling system of claim 1
wherein the inductive power emitter comprises a power feed line and a power return line,
wherein each one of one or more inductive emitter elements of the inductive power emitter comprises a section of the power feed line and a section of the power return line, and
wherein the system comprises a further inductive power emitter, and at least one connection member,
wherein the power feed line of the inductive power emitter is connected to the power return line of the further inductive power emitter via the connection member.

9. The antifouling system of claim 1, wherein the inductive power emitter comprises a ferrite material arranged within the system such that when the system is mounted to the object the ferrite material is between the object and the at least one inductive emitter element and/or the at least one inductive power receiver.

10. The antifouling system of claim 1, further comprising a coating material for application to the object, wherein the coating material has a relative permeability greater than 20.

11. The antifouling system of claim 1, further comprising a power source for delivering power to the inductive power emitter.

12. An object exposed to fouling conditions when in normal use, the object comprising an antifouling system of claim 1, wherein the inductive power emitter and the plurality of inductive power receivers are mounted on the object in a fixed configuration with respect to each other thereby to provide the inductive coupling.

13. The object of claim 12, wherein the antifouling system comprises:
a first panel including the inductive power emitter, and
a plurality of second panels, distinct from the first panel, each second panel comprising at least one of the plurality of inductive power receivers and at least one of the plurality of antifouling devices,
wherein the first panel and the plurality of second panels are mounted to the object such that different ones of the plurality of second panels are mounted at least partially to different areas of the object.

14. The object of claim 13,
wherein the object is for partial or complete submersion in water when in normal use,
wherein each one of the plurality of second panels includes one or more water resistant materials by which any of the plurality of inductive power receivers and any of the plurality of the antifouling devices present within that particular second panel are encapsulated for protecting them against water, and
wherein the object has a waterline and a part of the first panel is mounted such that it remains above the waterline when the object is in use so that a power source for providing power to the inductive power emitter can be connected to the inductive power emitter via a galvanic connection disposed above the waterline.

15. The object of claim 12, wherein the object comprises:
a ferrite material between the object and the at least one inductive emitter element and/or the at least one inductive power receiver; and/or
a coating material applied to the object, the coating material having a relative permeability greater than 20.

16. The antifouling system of claim 1,
wherein the object comprises the surface to be protected and an opposing surface,
wherein the inductive power receiver is situated on the surface to be protected, and
wherein the inductive power emitter is situated on the opposing surface.

17. The antifouling system of claim 1,
wherein the inductive power receiver and the inductive power receiver are situated on the surface to be protected.

18. An antifouling panel comprising:
a plurality of first inductive power receivers and a plurality of antifouling elements,
wherein the plurality of first inductive receivers are situated along a first edge of the panel, and
wherein the plurality of first inductive power receivers are configured to receive first power from a first inductive power emitter, distinct from the first inductive power receivers, that overlaps the plurality of first inductive power receivers, and
wherein the plurality of first inductive power receivers are configured to provide the first power to the at least a first one of the plurality of antifouling elements.

19. The antifouling panel of claim 18, further comprising a second plurality of inductive power receivers,
wherein the plurality of second inductive receivers are situated along a second edge of the panel, and
wherein the plurality of second inductive power receivers is configured to receive second power from a second inductive power emitter, distinct from the second inductive power receivers, that overlaps the plurality of second inductive power receivers, and
wherein the plurality of second inductive power receivers is configured to provide the second power to at least a second one of the plurality of antifouling elements.

20. The antifouling panel of claim 19,
wherein the first power is in phase with the second power, and
wherein the at least first one and the at least one second one of the plurality of antifouling elements are each configured to receive a portion of both the first power and the second power.

* * * * *